United States Patent [19]
Mitchell et al.

[11] Patent Number: 5,942,462
[45] Date of Patent: Aug. 24, 1999

[54] PROCESS FOR PREPARING GROUP 6 METAL-BASED OLEFIN POLYMERIZATION CATALYST COMPONENT

[75] Inventors: Jonathan P. Mitchell, Hastings on Hudson; Michael E. Villafane, White Plains, both of N.Y.

[73] Assignee: Akzo Nobel N.V., Netherlands

[21] Appl. No.: 08/796,726

[22] Filed: Oct. 20, 1997

[51] Int. Cl.$^6$ ............................. B01J 31/00; C07F 11/00
[52] U.S. Cl. ........................ 502/155; 502/152; 502/154; 502/156; 556/58; 556/63
[58] Field of Search ................... 502/151, 155, 502/156, 152; 556/58, 63

[56] References Cited

U.S. PATENT DOCUMENTS

| | | | |
|---|---|---|---|
| 5,117,020 | 5/1992 | Razavi | 556/43 |
| 5,418,200 | 5/1995 | Carney et al. | 502/117 |
| 5,593,931 | 1/1997 | Beach et al. | 502/117 |
| 5,641,871 | 6/1997 | Rohde et al. | 534/15 |

FOREIGN PATENT DOCUMENTS

| | | | |
|---|---|---|---|
| 832476 | 1/1970 | Canada | 260/435 |
| 222619 | 5/1987 | European Pat. Off. | |
| 509294 | 10/1992 | European Pat. Off. | |
| 2070452 | 9/1971 | France | 556/63 |
| 45-35534 | 11/1970 | Japan | 556/58 |
| 49-39244 | 10/1974 | Japan | 556/58 |
| 349219 | 8/1975 | U.S.S.R. | 502/156 |
| 2271116 | 4/1994 | United Kingdom. | |
| 96/23006 | 8/1996 | WIPO. | |
| WO 96/27621 | 9/1996 | WIPO. | |

OTHER PUBLICATIONS

Inorganic Synthesis, H. Holtzclaw, Jr., ed., vol. VIII, pp. 150–151, McGraw–Hill, New York, 1966.

H.H. Zeiss et al., Angew. Chem. Int. Ed. Engl., vol. 6, No. 5, p. 435, 1967.

Derwent Patent Abstract 50514S–AE (1971).

J.C. Fettinger et al., "Accessibility of 17–Electron Structures for Cyclopentadienylchromium(III) Compounds. 1. Experimental Studies on the Dichloride and Dimethyl Compounds", Organometallics 1996, 15, 4211–4222.

K.H. Theopold, "Organochromium(III) Chemistry: A Neglected Oxidation State", Acc. Chem. Res. 1990, 23, 263–270.

Y. Liang, et al. "Constrained Geometry Chromium Catalysts for Olefin Polymerization", Organometallics 1996, 15, 5284–5286.

S.K. Noh et al., "[(Cp*(Me)Cr($\mu$–Me)]$_2$: An Electron–Deficient Chromium(III) Alkyl with Bridging Methyl Groups and a Cr—Cr Bond", J. Am. Chem. Soc. 1989, 111, 9127–9129.

*Primary Examiner*—Mark L. Bell
*Assistant Examiner*—J. Pasterczyk
*Attorney, Agent, or Firm*—Richard P. Fennelly

[57] ABSTRACT

A Group 6 metal-containing, ligand-containing olefin polymerization catalyst component can be made by using an unsolvated Group 6 metal trihalide as the starting reagent for the Group 6 metal which comprises contacting (e.g., in tetrahydrofuran) the Group VIB metal trihalide, such as chromium trichloride, with a ligand reagent or reagents, such as a cyclopentadienyl-containing lithium compound and a lower alkyl-containing lithium compound, in the presence of a sigma donor ligand, such as pyridine.

7 Claims, No Drawings

PROCESS FOR PREPARING GROUP 6 METAL-BASED OLEFIN POLYMERIZATION CATALYST COMPONENT

BACKGROUND OF THE INVENTION

Chromium based catalysts are used in the commercial polymerization of small alpha olefins such as ethylene and propylene. U.S. Pat. No. 5,418,200 to Carney et. al. describes a series of Group 6 metal-based ligand-containing olefin polymerization catalyst components which when in combination with a suitable cocatalyst and supported on an inorganic metal oxide or inorganic metal phosphate produce high productivity alpha-olefin polymerization catalysts. The present invention relates to an improved process for preparing such Group 6 metal-based, ligand-containing olefin polymerization catalyst components. For example, the half-sandwich chromium-based olefin polymerization catalyst component, $Cp^*Cr(CH_3)_2$ (pyr), where $Cp^*$ designates the radical $C_5Me_5$ and pyr designates pyridine can be produced in high yield and in a pure form. This represents a significant advantage of the current invention over the type of synthetic procedure known to persons in the art. Previously published syntheses of $Cp^*Cr(Me_2)$ (pyr), for example, as described in Example 15 of U.S. Pat. No. 5,418,200 to Carney et al. and in S. K. Noh et al., J. Am. Chem. Soc. 1989, 111, 9127, require the use of the starting material $CrCl_3 (THF)_{31}$, where THF designates tetrahydrofuran. This starting material must be synthesized, typically by a Soxhlet extraction of $CrCl_3$ with Zn metal in refluxing THF. This is both tedious to perform as well as difficult to scale up for commercial synthesis in order to produce $CrCl_3(THF)_3$ of sufficient purity for subsequent catalyst component synthesis. The current invention (as typified by Example 1) removes this synthetic stage and uses commercially available $CrCl_3$ as the starting material for the catalyst synthesis.

SUMMARY OF THE INVENTION

A process for preparing a Group 6 metal-based, ligand-containing olefin polymerization catalyst component using a Group VIB metal trihalide as the starting reagent for the Group VIB metal which comprises contacting the Group VIB metal trihalide with the ligand reagent or reagents in the presence of a sigma donor stabilizing ligand.

DESCRIPTION OF THE PREFERRED EMBODIMENTS

In the process of the present invention, a Group 6 metal trihalide is an essential reagent. It is preferred that the trichlorides be utilized with the preferred Group 6 metal being chromium, although other trihalides, such as the tribromides and the triiodides, can also be selected for use.

The starting material is contacted with reagents for the other desired ligands on the final catalyst component in the presence of a sigma donor stabilizing ligand. The reagents which are used to provide some of the other hydrocarbyl ligands include hydrocarbyl lithium compounds, hydrocarbyl potassium compounds, hydrocarbyl magnesium compounds and hydrocarbyl silyl compounds, of which hydrocarbyl lithium compounds are preferred. Representative reagents include cyclopentadienyl-containing lithium compounds, of the type described in U.S. Pat. No. 5,418,200 to Carney at Col. 4, lines 19 to 31, wherein the preferred species is pentamethylcyclopentadienyl lithium, and cyclopentadienyl amide-containing lithium compounds, of the type described in Y. Liang et. al. Organometallics, 1996, 15, 5284, wherein the preferred species is $Li_2(THF)$ $[Me_4C_5SiMe_2N^tBu]_n$ and also the lower hydrocarbyl lithium compounds, of the type described in U.S. Pat. No. 5,418,200 to Carney at Col. 4, lines 46 to 59. Also used in the present process is a sigma donor stabilizing ligand of the type described in U.S. Pat. No. 5,418,200 to Carney at Col. 4, line 60 to Col. 5, line 2, wherein the preferred species include the ether, tetrahydrofuran, and the amine, pyridine.

Examples of such Group 6 catalyst components that can be made by the present invention are described in U.S. Pat. No. 5,418,200 to Carney at Col. 5, lines 3 to 39, in PCT International Patent Publication No. WO 96/23006 in Examples 2 and 4, and in PCT International Patent Publication No. WO 96/27621 at Col. 14, lines 17 to 21.

The process of the present invention can be advantageously conducted by first contacting the Group 6 metal trihalide with an ether solvent, such as tetrahydrofuran, followed by reaction of the cyclopentadienyl-containing reagent, either as a solid or in an ether solvent, preferably at temperatures of from about $-20°$ C. to about ambient temperature. The resulting product may then be reacted, for example, at ambient temperature, with a suitable sigma donor ligand, and then, preferably, at temperatures of from about $-20°$ C. to about ambient temperature, with the lower hydrocarbyl-containing reagent to produce the final end product.

Combination of the thus produced catalyst component with the other cocatalytic compound (either an aluminoxane or Group 2 or 13 alkyl compound) will produce the final catalyst that may be supported on, for example, silica, alumina, aluminum phosphate, or alumina aluminum phosphate.

The present invention is further illustrated by the Example which follow. In the following Examples, all manipulations were conducted under nitrogen using standard glove box or Schlenk line techniques. All solvents were thoroughly dried and degassed prior to use.

EXAMPLE 1

Synthesis of $Cp^*CrMe_2(pyr)$ from $CrCl_3$

In a 5 liter flask, $CrCl_3$ (136.6 g, 0.86 mol) and 750 ml of THF were combined to give a purple slurry which was subsequently cooled to $0°$ C. using ice. In a separate 2 liter flask, $Cp^*Li$ (122.6 g, 0.86 mol) and 1.25 liters of chilled THF were combined at $0°$ C. The chilled $Cp^*Li$ slurry was then added dropwise over a period of one hour to the chilled $CrCl_3$ slurry. The resulting composition was allowed to warm to room temperature, and the resulting blue solution was stirred for sixteen hours.

At room temperature, pyridine (71.6 g, 1.00 mol, 1.05 equiv.) was then added dropwise over thirty minutes to the previously formed composition, resulting in the deposition of blue crystals. This mixture was stirred at room temperature for a further three hours before being cooled again to $0°$ C. To this mix was then added an ethereal methyllithium solution (902.1 g, 1.4 M, 1.72 mol, 2.00 equiv.) over a period of one hour. The resulting dark brown mixture was allowed to warm to room temperature and was stirred for sixteen hours. Volatiles were then removed in vacuo to give a dark brown solid.

The crude product was extracted from the LiCl byproduct using diethyl ether. Recrystallization gave dark brown crystals which were isolated and dried in vacuo. The total yield of $Cp^*Cr(Me)_2(pyr)$ was 193.1 g, 0.65 mol, 76%.

Comparative Example 2

Synthesis of Cp*Cr(Me)$_2$(pyr) from CrCl$_3$(THF)$_3$ (I) Synthesis of CrCl$_3$(THF)$_3$ CrCl$_3$(THF)$_3$ was synthesized according to the Soxhlet extraction procedure given by J. P. Collman et al., Inorganic Syntheses, 1966, Vol. 8, 150. The use of 26.34 g of CrCl$_3$ and 2.6 g of Zn in 300 ml of tetrahydrofuran yielded 34.85 g of CrCl$_3$(THF)$_3$ (56% based on CrCl$_3$).

(ii) Synthesis of Cp*Cr(Me)$_2$(pyr)

CrCl$_3$(THF)$_3$ (30.00 g, 80.1 mmol) and 250 ml THF were combined to give a purple slurry. In a separate flask, Cp*Li (11.38 g, 80.0 mmol) and 150 ml THF were combined. The Cp*Li slurry was then added dropwise to the CrCl$_3$(THF)$_3$ slurry. The Cp*Li was washed with a further 150 ml of THF, and this was added to the reaction mixture. The resulting composition was then stirred at room temperature for one and one half hours.

Pyridine (6.65 g, 84.1 mmol, 1.05 equivalents) was added dropwise to the previous product, resulting in the deposition of blue crystals. This mixture was stirred at room temperature for a further hour before addition of an ethereal MeLi solution (83.81 g, 1.4 M, 160.3 mmol, 2.00 equivalents). The resulting dark brown mixture was allowed to stir at room temperature for thirty minutes before volatiles were removed in vacuo.

The crude product was extracted from the LiCl byproduct using heptane. Recrystallization gave dark brown crystals which were isolated and dried in vacuo. A second batch of crystals was isolated by exhaustive extraction using pentane and subsequent recrystallization. The total yield of Cp*Cr(Me)$_2$(pyr) was 10.13 g, 34.1 mmol, 43% based on CrCl$_3$(THF)$_3$.

The foregoing Examples merely illustrates a particular embodiment of the present invention in comparison with a prior art technique and, for that reason, should not be construed in a limiting sense. The scope of protection desired is set forth in the Claims which follow.

We claim:

1. A process for preparing a Group 6 metal-containing, ligand-containing olefin polymerization catalyst component using an unsolvated Group 6 metal trihalide as the starting reagent for the Group 6 metal-containing component, which comprises contacting said unsolvated Group 6 metal trihalide with a cyclopentadienyl-containing ligand reagent with a sigma donor stabilizing ligand as the solvent during said contacting.

2. A process as claimed in claim 1 wherein the unsolvated Group 6 metal trihalide is chromium trichloride.

3. A process as claimed in claim 1 wherein the unsolvated Group 6 metal trihalide is chromium trichloride and the ligand reagent is a cyclopentadienyl-containing lithium compound.

4. A process as claimed in claim 1 wherein the unsolvated Group 6 metal trihalide is chromium trichloride and the ligand reagent is C$_5$Me$_5$Li.

5. A process as claimed in claim 1 wherein pyridine is added after said contacting as a further sigma donor stabilizing ligand.

6. A process as claimed in claim 1 wherein the unsolvated Group 6 metal trihalide is chromium trichloride, the ligand reagent is C$_5$Me$_5$Li, and pyridine is added after said contacting as a further sigma donor stabilizing ligand.

7. A process as claimed in claim 1 wherein the unsolvated Group 6 metal trihalide is chromium trichloride, the ligand reagent is C$_5$Me$_5$Li, pyridine is added after said contacting as a further sigma donor stabilizing ligand, and the contacting is conducted in tetrahydrofuran solvent.

* * * * *